United States Patent [19]

Murtha et al.

[11] 4,115,204
[45] Sep. 19, 1978

[54] SEPARATION OF PHENOL-, CYCLOHEXANONE-, AND CYCLOHEXYLBENZENE-CONTAINING MIXTURES EMPLOYING AN N,N-DISUBSTITUTED AMIDE

[75] Inventors: Timothy P. Murtha; Ernest A. Zuech, both of Bartlesville, Okla.

[73] Assignee: Phillips Petroleum Company, Bartlesville, Okla.

[21] Appl. No.: 817,764

[22] Filed: Jul. 21, 1977

[51] Int. Cl.$^2$ .................. B01D 3/40; C07C 39/04; C07C 45/24
[52] U.S. Cl. .................. 203/60; 203/84; 260/586 R; 568/757
[58] Field of Search .................. 203/60, 57, 51, 38, 203/84; 260/586 R, 586 P, 621 A, 621 C

[56] References Cited

U.S. PATENT DOCUMENTS

| | | | |
|---|---|---|---|
| 2,762,760 | 9/1956 | Walker | 260/621 A |
| 3,515,762 | 6/1970 | Koide et al. | 203/60 |
| 3,707,575 | 12/1972 | Muller et al. | 203/60 |
| 4,016,049 | 4/1977 | Fozzard et al. | 203/60 |
| 4,019,965 | 4/1977 | Fozzard | 203/60 |
| 4,021,490 | 5/1977 | Hudson | 260/621 C |

*Primary Examiner*—Wilbur L. Bascomb, Jr.

[57] ABSTRACT

Phenol-, cyclohexanone-, and cyclohexylbenzene-containing mixtures are extractively distilled to provide overhead of cyclohexanone and a kettle product substantially free of cyclohexanone by employing an N,N-disubstituted amide. When substantially no cyclohexylbenzene is present in the mixture to be extractively distilled, the kettle product will be essentially composed of the amide and phenol.

3 Claims, 1 Drawing Figure

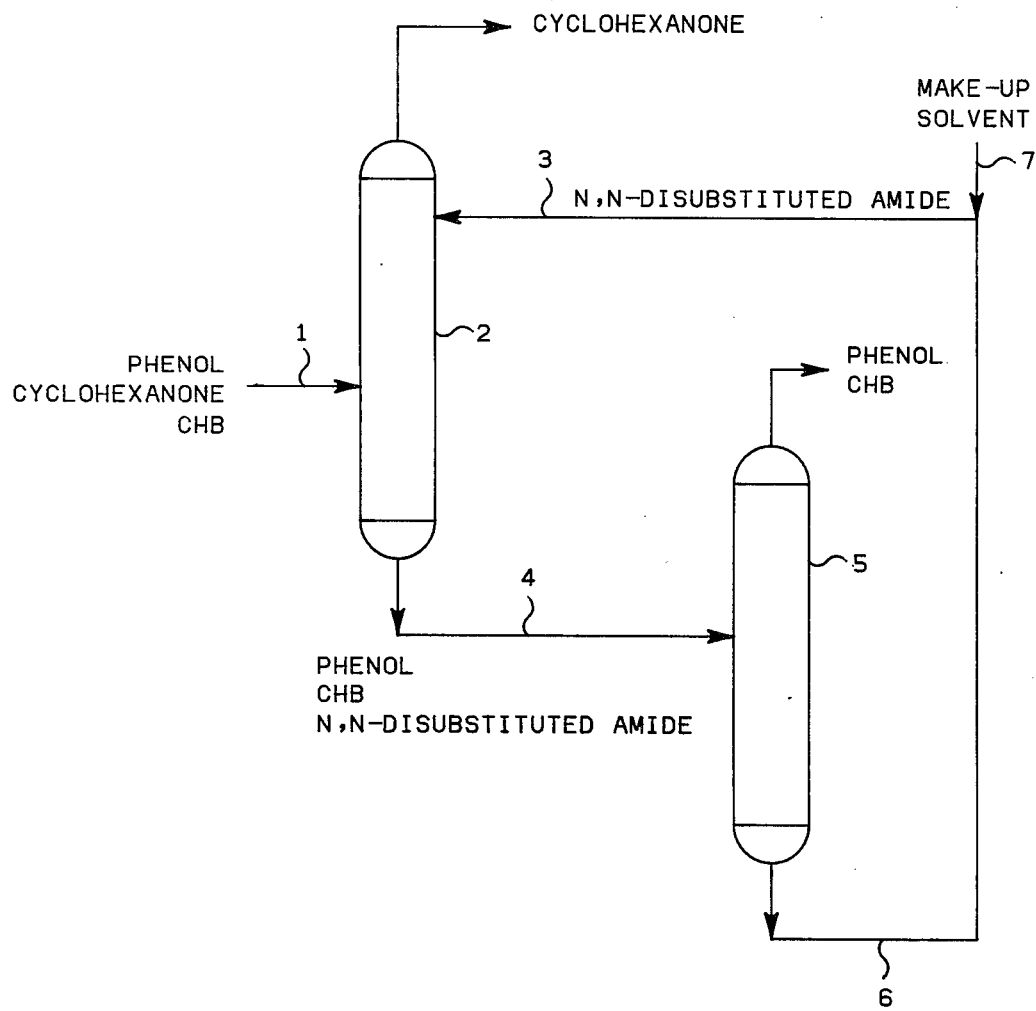

SEPARATION OF PHENOL-, CYCLOHEXANONE-, AND CYCLOHEXYLBENZENE-CONTAINING MIXTURES EMPLOYING AN N,N-DISUBSTITUTED AMIDE

This invention relates to separation of phenol from its azeotropes, including phenol-cyclohexanone azeotrope, which may be in the presence of cyclohexylbenzene. In one of its aspects, the invention relates to the recovery of phenol and cyclohexanone from the cleavage products resulting from cleavage of the oxidation product of cyclohexylbenzene to provide cyclohexylbenzene hydroperoxide which then is converted to produce the phenol, cyclohexanone, and any unreacted cyclohexylbenzene.

In one of its concepts, the invention provides a process for extractive distillation of a mixture containing phenol and cyclohexanone employing as an agent an N,N-disubstituted amide. In another of its concepts, the invention provides such a process for extractive distillation of a mixture containing phenol, cyclohexanone, and cyclohexylbenzene resulting from cleavage of the oxidation product of cyclohexylbenzene, i.e., cyclohexylbenzene hydroperoxide.

In a further concept of the invention, the extractive distillation yields an overhead product of high purity cyclohexanone of the order of about 98 weight percent.

In a still further concept of the invention, the extractive distillation bottoms product which will consist essentially of phenol and the agent, as well as any cyclohexylbenzene which may have been present, is subjected to distillation to recover phenol and any cyclohexylbenzene as an overhead and the amide as bottoms which are reused as agent or solvent in the extractive distillation.

It is an object of this invention to separate mixtures containing phenol and cyclohexanone which also can contain cyclohexylbenzene. It is another object of this invention to provide an extractive distillation agent or solvent to separate mixtures as herein described. It is a still further object of the invention to provide an extractive distillation operation comprising a mixture of one or more agents or solvents also described herein.

Other aspects, concepts, objects, and the several advantages of the invention are apparent from a study of this disclosure and the appended claims.

According to the present invention, a mixture containing phenol and cyclohexanone, which mixture may contain cyclohexylbenzene, is extractively distilled and thus separated to produce as an overhead product a fraction containing essentially cyclohexanone and a kettle product containing phenol, cyclohexylbenzene when present, and the agent or solvent.

Cyclohexylbenzene (CHB) can be converted to phenol and cyclohexanone via cyclohexylbenzene hydroperoxide. The acid catalyzed cleavage of cyclohexylbenzene hydroperoxide in the presence of unoxidized CHB results in a mixture of CHB, phenol, and cyclohexanone. This mixture is difficult to separate by conventional distillation techniques because phenol and cyclohexanone form an azeotrope (bp 184° C. at atmospheric pressure) containing about 72 weight percent phenol. In addition, CHB codistills with this azeotrope.

Mixture to be Separated

Any mixture of phenol, cyclohexanone, and CHB or mixture of phenol and cyclohexanone can be separated in the process of the invention.

It is within the scope of this invention to remove by suitable methods a portion of any of the components from the mixture to be separated prior to the extractive distillation with an N,N-disubstituted amide. For example, any excess of cyclohexanone over the quantity present in the azeotrope can be first distilled from the mixture as an essentially pure material. Since CHB codistills with the phenol/cyclohexanone azetrope in quantities of about 2 to 10 weight percent, any excess of CHB over that amount can be removed by fractional distillation to take the phenol/cyclohexanone mixture containing about 2 to 10 weight percent CHB overhead. It is also within the scope of this invention to remove essentially all of the CHB from the mixture by suitable techniques, such as extractive distillation, prior to the extractive distillation of this invention.

Solvent

The N,N-disubstituted amide solvent which can be used in the extractive distillation of this invention can contain up to 30 carbon atoms and can be represented by the following general formula:

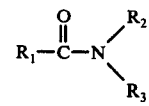

wherein $R_1$, $R_2$, and $R_3$ are each selected from the group consisting of alkyl radicals containing 1 to 20 carbon atoms, cycloalkyl radicals containing 5 to 20 carbon atoms, aryl or substituted aryl radicals containing 6 to 12 carbon atoms with the substituent groups being one or more or a mixture of alkyl, alkoxy, cycloalkyl, halogen, or the like, and aralkyl radicals containing 7 to 12 carbon atoms. The N,N-disubstituted amide solvent selected has a boiling point above the boiling point of phenol (182° C. at atmospheric pressure) to facilitate the separation of the solvent for recycling by fractional distillation. For ease of handling, it is preferred that the solvent be a liquid or a low melting (below about 80° C.) solid. A mixture of amides can be used.

Specific examples of suitable solvents include N,N-diethyldodecanamide, N,N-dibutyldodecanamide, N-methyl-N-butyldodecanamide, N,N-diethyltetradecanamide, N,N-dicyclohexyldecanamide, N,N-dibutylbenzamide, N,N-dibenzyloctanamide, and the like. These compounds are either commercially available or can be prepared by known reactions. For example, N,N-diethyldodecanamide can be prepared from diethylamine and dodecanoic acid.

Extractive Distillation Conditions

The extractive distillation of this invention can be carried out under a variety of conditions. The volume ratio of N,N-disubstituted amide solvent to feedstream will be broadly from 0.1/1 to 10/1, preferably 1/1 to 5/1. To avoid possible thermal decomposition or other reactions during the extractive distillation, head temperatures below 135° C., preferably below 100° C., are used with a reduced pressure sufficient to allow the separation to occur.

Referring to the flow diagram which further illustrates the process of this invention, a mixture consisting essentially of phenol, cyclohexanone, and CHB is passed by 1 to an extractive distillation column 2. The N,N-di-substituted amide solvent or mixture of solvents is introduced into the extractive distillation colume 2 by 3 at a point above the point of introduction of the mixture to be separated.

A vaporous overhead stream consisting essentially of cyclohexanone is withdrawn from the extractive distillation column 2. A liquid bottoms stream consisting essentially of phenol, CHB, and N,N-disubstituted amide is withdrawn from the extractive distillation column 2 by 4 and passed to distillation column 5.

In the distillation column 5, the phenol-CHB-N,N-disubstituted amide mixture is separated into a vaporous overhead stream consisting essentially of phenol and CHB and a liquid bottom stream consisting essentially of N,N-disubstituted amide which is passed by 6 and 3 to the extractive distillation column 2. Makeup N,N-disubstituted amide is added by 7 if necessary. The phenol-CHB overhead stream can be passed to another separation stage to separate the mixture.

When the mixture to be separated consists essentially of phenol and cyclohexanone, the bottom stream from extractive distillation column 2 will consist essentially of phenol and N,N-disubstituted amide and the overhead stream from distillation column 5 will consist essentially of phenol.

EXAMPLES

In the following examples extractive distillations were conducted in an electrically heated 0.75" (19 mm) × 36" (914 mm) column containing 0.25" (6.4 mm) Por-Pak stainless steel perforated screen packing. The solvent was fed through a rotameter and heating section to an introduction port 3" (76 mm) from the top of the column. The mixture to be separated was fed through a rotameter and heating section to an introduction port 18" (457 mm) from the top of the column. The overhead and kettle products were collected and then analyzed by gas-liquid phase chromatography (glpc) on a Hewlett Packard 5710A chromatograph equipped with a flame ionization detector.

The mixtures to be separated were prepared from commercial, reagent grade phenol and cyclohexanone and cyclohexylbenzene (98% purity) prepared by the reductive alkylation of benzene.

EXAMPLE I

Two runs (Runs 1 and 2) were carried out according to the invention utilizing N,N-diethyldodecanamide as the solvent for the extractive distillation of a mixture containing 68 weight percent phenol, 27 weight percent cyclohexanone, and 5 weight percent CHB.

The extractive distillation conditions in Run 1 were 50 mm Hg pressure, 59°-65° C. head temperature, and a 2.5/1 solvent/feed volume ratio. Over a 7-hour run time, the overhead fractions contained cyclohexanone having an average purity of 97.6 weight percent. The cyclohexanone collected was 88.6 weight percent of the amount of cyclohexanone fed to the column during the run.

The kettle fraction (phenol, CHB, N,N-diethyldodecanamide, and a low level of cyclohexanone) from the above extractive distillation was fractionally distilled in an electrically heated 0.75" (19 mm) × 8" (203 mm) column containing perforated stainless steel packing. The overhead fractions were collected and analyzed by glpc and found to contain mainly phenol and cyclohexanone and N,N-diethyldodecanamide (1.1 to 1.6 weight percent). The kettle product was essentially pure N,N-diethyldodecanamide.

Run 2 was conducted like Run 1 except that the head temperature was 59°-60° C. and the solvent/feed volume ratio was increased to 2.7/1. Over a three-hour run time, the overhead fractions contained cyclohexanone with an average purity of 98.3 weight percent. The cyclohexanone collected was 98.4 weight percent of the amount fed to the column during the run.

The results of these runs shown that N,N-diethyldodecanamide successfully separates cyclohexanone in high yield and high purity from a mixture of phenol, cyclohexanone, and CHB and that the N,N-diethyldodecanamide solvent can be recovered for recycle.

EXAMPLE II

Two runs (Runs 3 and 4) were carried out according to the invention utilizing N,N-diethyldodecanamide as the solvent for the extractive distillation of a mixture containing phenol and cyclohexanone.

Run 3 was conducted with a mixture containing 70 weight percent phenol and 30 weight cyclohexanone. The conditions were 50 mm Hg pressure, 58°-62° C. head temperature, and a 2.8/1 solvent/feed volume ratio. Over a 7-hour run time, the overhead fractions contained cyclohexanone with an average purity of 98 weight percent. The cyclohexanone collected was 96.8 weight percent of the amount fed to the column during the run.

Run 4 was conducted with a mixture containing 50 weight percent phenol and 50 weight percent cyclohexanone. The conditions were the same as in Run 3 except that the head temperature was 60°-62° C. and the solvent/feed volume ratio was 2.2/1. Over a 2.5-hour run time, the overhead fractions contained cyclohexanone with an average purity of 99.6 weight percent. The cyclohexanone collected was 97.3 weight percent of the amount fed to the column during the run.

The results of these runs show that N,N-diethyldodecanamide successfully separates cyclohexanone in high yield and high purity from a mixture of phenol and cyclohexanone.

EXAMPLE III

In a control run, an extractive distillation of a mixture containing 68 weight percent phenol, 27 weight percent cyclohexanone, and 5 weight percent CHB was conducted with phenyl salicylate as solvent. The conditions were 80 mm Hg pressure, 85°-93° C. head temperature, and a solvent/feed ratio of 3.06/1 Over a three-hour run time, the overhead product contained 58.3 weight percent of the cyclohexanone fed to the column with a purity of 33.9 weight percent.

This extractive distillation was repeated with the same solvent, but with the present increased to 100 mm Hg, the head temperature increased to 99°-102° C., and the solvent/feed ratio increased to 3.2/1. Over a 4-hour run time, the overhead product contained 90.6 weight percent of the cyclohexanone fed to the column with a purity of 25.9 weight percent.

Thus, phenyl salicylate, a solvent outside the scope of this invention, does not cleanly separate cyclohexanone from the mixture of cyclohexanone, phenol, and CHB.

EXAMPLE IV

In another control run, an extractive distillation of a mixture containing 70 weight percent phenol and 30 weight percent cyclohexanone was conducted with methyl oleate as solvent. The conditions were 100 mm Hg pressure, 53°–73° C. head temperature, and a solvent/feed volume ratio of 4.2/1. Over a seven-hour run time, the overhead fractions contained 48.1 weight percent of the cyclohexanone fed to the column with a purity of 94.7 weight percent.

Thus, methyl oleate, a solvent outside the scope of this invention, does not cleanly remove cyclohexanone from a mixture of phenol and cyclohexanone.

Reasonable variation and modification are possible within the scope of the foregoing disclosure and the appended claims to the invention the essence of which is that there has been found that extractive distillation of a mixture of phenol and cyclohexanone, and cyclohexylbenzene when it is present, can be accomplished with good yields of high purity cyclohexanone as overhead employing an N,N-disubstituted amide solvent as herein described.

We claim:

1. An extractive distillation of a mixture containing phenol and cyclohexanone, which mixture may also contain cyclohexylbenzene, which comprises distilling said mixture in the presence of a solvent comprising at least one N,N-disubstituted amide which contains up to 30 carbon atoms and can be represented by the following general formula

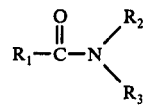

wherein $R_1$, $R_2$, and $R_3$ are each selected from the group consisting of alkyl radicals containing 1 to 20 carbon atoms, cycloalkyl radicals containing 5 to 20 carbon atoms, aryl or substituted aryl radicals containing 6 to 12 carbon atoms with the substituent groups being one or more or a mixture of alkyl, alkoxy, cycloalkyl, halogen, or the like, and aralkyl radicals containing 7 to 12 carbon atoms, the N,N-disubstituted amide solvent selected has a boiling point above the boiling point of phenol (812° C. at atmospheric pressure), and mixtures thereof.

2. A process according to claim 1 wherein the selected solvent is one or more of the following: N,N-diethyldodecanamide, N,N-dibutyldodecanamide, N-methyl-N-butyldodecanamide, N,N-diethyltetradecanamide, N,N-dicyclohexyldecanamide, N,N-dibutylbenzamide, and N,N-dibenzyloctanamide.

3. A process according to claim 1 wherein there is recovered as an overhead product cyclohexanone and a kettle product containing solvent and phenol and when it is present cyclohexylbenzene, the keettle product is distilled to recover phenol and any cyclohexylbenzene therefrom thus recovering the solvent which then can be reused.

* * * * *